United States Patent [19]

Melaja et al.

[11] 4,066,711
[45] Jan. 3, 1978

[54] METHOD FOR RECOVERING XYLITOL

[75] Inventors: Asko J. Melaja; Jouko J. Virtanen; Heikki O. Heikkila, all of Kantvik, Finland

[73] Assignee: Suomen Sokeri Osakeyhtio (Finnish Sugar Company), Helsinki, Finland

[21] Appl. No.: 666,584

[22] Filed: Mar. 15, 1976

[51] Int. Cl.² ............................................. C07C 29/24
[52] U.S. Cl. ................................................. 260/637 R
[58] Field of Search ............ 260/635 C, 637 R, 643 G

[56] References Cited

U.S. PATENT DOCUMENTS

| | | | |
|---|---|---|---|
| 2,524,414 | 10/1950 | Wolfrom et al. | 260/637 R |
| 2,989,569 | 6/1961 | Apel | 260/635 C |
| 3,021,374 | 2/1962 | Radzitzky | 260/643 G |
| 3,586,537 | 6/1971 | Steiner et al. | 260/635 C |
| 3,627,636 | 12/1971 | Jaffe et al. | 260/635 C |
| 3,692,582 | 9/1972 | Melaga | 127/46 A |

OTHER PUBLICATIONS

Samuelson et al., "Acts Chemics Scandinavica", zz (1968), pp. 1252–1258.

Primary Examiner—Joseph E. Evans
Attorney, Agent, or Firm—Brumbaugh, Graves, Donohue & Raymond

[57] ABSTRACT

A method for preparing pharmaceutical grade xylitol from an aqueous solution containing mixtures of polyols including xylitol which comprises subjecting the solution to a crude crystallization and recrystallization of xylitol followed by the recovery of residual xylitol from the mother liquor by fractionating the solution using at least two columns of ion-exchange resin in two different metal forms.

10 Claims, 5 Drawing Figures

Scheme for xylitol production by double crystallization combined with removal of microcrystalline galactitol and syrups fractionation Yield 96% of xylitol
Water evaporated 25 kg/kg xylitol
Material balance in Table II
Water amounts correspond to the material balance in Table II Scheme for xylitol production by double crystallization combined with removal of microcrystalline galactitol and syrups fractionation Yield 96% of xylitol
Water evaporated 25 kg/kg xylitol
Material balance in Table III
Water amounts correspond to the material balance in Table III

METHOD FOR RECOVERING XYLITOL

Xylitol may be prepared from xylose-containing materials by hydrogenation of the materials to form xylitol, followed by crystallization of the xylitol therefrom. Hemicellulose hydrolysates are usually used as raw materials. Prior art methods for the preparation of xylitol are described, for example, in British Pat. Nos. 1,209,960, 1,236,910, and 1,273,498, each of which disclose methods for the hydrolysis of hemicellulose materials followed by purification of the hydrolysate. South African Pat. No. 73/7731 also discloses a method for the crystallization of xylitol from an aqueous reaction medium in which xylitol is formed by the reduction of xylose. As additional prior art, the Applicants acknowledge a Russian article by Lejkin et al., *Proizvostro Ksilita* (Production of Xylitol, Moscow, 1962) which gives a review of a processes known at that time. Additional references dealing with prior art processes include U.S. Pat. Nos. 3,212,932 and 3,558,725.

It has previously been found that pure xylitol can be prepared from polyol solutions which contain several other polyols as impurities. One such process is described in copending U.S. patent application Ser. No. 588,022, filed June 18, 1975. In that application, the polyol solution is subjected to chromatographic fractionation on a column filled with a suitable ion-exchange resin. Pure xylitol is crystallized from a purified xylitol-containing fraction obtained by the chromatographic fractionation technique.

The method described in the aforementioned copending application has certain disadvantages. In order to obtain pharmaceutical grade xylitol by crystallization from water solution, the percentage of xylitol in the crystal mass must be at least 85% on a dry solids basis. Because galactitol is considered to be a harmful impurity in xylitol, it must be nearly completely removed in order to make an acceptable pharmaceutical grade crystaline xylitol. Specifications require that pharmaceutical grade xylitol contain less than 0.2% galactitol. In order to achieve this high purity level in the crystals, the solution from which the xylitol is crystallized must contain no more than 1.5% galactitol on a dry substance basis. When the raw solution contains large amounts of galactitol, low yields of xylitol result. Removal of sufficient galactitol during the prior art chromatographic fractionation of the polyol solution requires great dilution of the solutions and greatly reduces the capacity of a given system.

It has now been found that the yield of recoverable pharmaceutical grade xylitol from solutions of mixed polyols is greatly increased by utilizing a method which comprises (a) removing a major portion of the xylitol from the polyol solution by crude crystallization followed by recrystallization while reserving the mother liquor and combining the washing liquids therewith, (b) recovering galactitol from the surfaces of the xylitol crystals and the combined mother liquor and crystal washing liquids in the form of microcrystals, and (c) thereafter chromatographically fractionating said combined mother liquor and washing liquids by passing them through an ion-exchange chromatographic column to recover xylitol. In a preferred embodiment, two parallel columns of ion-exchange resins, one column containing the resin in an alkaline-earth form and the other in $Al^{+++}$ or $Fe^{+++}$ form are used to recover xylitol. In addition, the mother liquor from the recrystallization step together with washing liquids therefrom, if any, may be returned to the system by combining them with the feed of mixed polyols just prior to the crude crystallization step.

The raw materials which may be hydrolized to obtain a mixture of polyols useful as a starting material for the practice of the process of the present invention include lignocellulose materials including wood of various species of trees, such as birch and beech. Also useful are oat hulls, corn cobs and stalks, coconut shells, almond shells, straw, bagasse and cotton seed hulls. Where wood is used, it is preferably subdivided into chips, shavings, sawdust, and the like. In addition, xylan-rich prehydrolysates from wood-chemical industries can be used. These are waste by-products and contain the main part of wood hemicellulose. The prehydrolysates are hydrolyzed with dilute mineral acid to liberate xylose and the salts and acids may be thereafter removed by ion-exclusion or ion-exchange techniques.

Suitable procedures for obtaining mixtures of polyols from these materials are described, for example, in U.S. Pat. Nos. 2,734,136, 2,759,856, 2,801,939, 2,974,067, and 3,212,932. The important consideration is selecting the appropriate method of hydrolysis is that a maximum yield of pentoses be obtained and that the resulting pentose-rich solution be neutralized using materials such as sodium hydroxide which do not cause serious deterioration of sugars. Where the pentose material is obtained by methods other than acid hydrolysis, a step of desalting by ion-exclusion as described below may not be required.

In accordance with the next stage, again one known in the art, a purification of the hydrolysate is accomplished using two main steps; one is removal of the salt, sodium sulfate, and the major part of the organic impurities and coloring bodies with ion-exclusion techniques, while a second stage accomplishes final color removal. Suitable ion-exclusion techniques which removes salt from the solution are described in U.S. Pat. Nos. 2,890,972 and 2,937,959. Similar processes have been used in the sugar industry for the purification of molasses.

The second stage of final color removed is carried out by treating the impure solutions with an ion-exchange system consisting of a strong cation exchanger followed by a weak anion exchanger and then followed by a step of passing the solution through an adsorbent or activated carbon bed. These methods are also known in the sugar industry. One such procedure is described, for example, in U.S. Pat. No. 3,558,725. Other pertinent disclosures of this feature include J. Stamberg and V. Valter: Entfarbungsharze, Akademie Verlag Berlin 1970; P. Smit: Ionenaustauscher und Adsorber bei der Herstellung und Reiningung von Zuckern, Pektinen und verwandten Stoffen. Akademie Verlag Berlin 1969; J. Hassler: Activated carbon; Leonard Hill London 1967.

The purification step may be further improved where necessary by the addition of a step which uses a synthetic macroreticular adsorbent such as Amberlite XAD 2 to remove organic impurities. The macroreticular adsorbent can be used in the purification stage immediately following the ion-exclusion step but prior to the cation exchanger. Alternatively, it can be the final step of the purification stage.

The purified pentose solution is then hydrogenated and treated in a manner similar to the hydrogenation of glucose to sorbitol. One such suitable process is described in an article by W. Schnyder entitled "The Hydrogenation of Glucose to Sorbitol with Raney Nickel Catalyst", Dissertation at the Polytechnical Institute of Brooklyn, 1962.

By following the above described prior art processes, solutions are obtained which are hemicellulose hydrolysates that have been purified and hydrogenated to provide a mixture of polyols containing a high level of xylitol. It is these solutions that are preferably used as the raw material in the process of the present invention.

The preferred ion-exchange resins used in the present invention are of the type described as sulfonated polystyrene cation exchange resins cross-coupled with divinyl benzene. The alkaline earth metal salts of these resins, such as the calcium, barium and strontium form, provide acceptable results and of these, the strontium form gives the best separation of the polyols. A significant improvement in the separation of certain polyols is obtained where the trivalent metal forms such as the $Al^{+++}$ and $Fe^{+++}$ are used. It has been found, for example, that the $Al^{+++}$ and $Fe^{+++}$ forms of the resin provide advantages over the use of the alkaline earth metal forms by themselves. The polyols are eluted from the $Al^{+++}$ and $Fe^{+++}$ forms of the resin in a different order. This is important because separation of the major impurity, sorbitol, can thus be improved. In the second place, in the recovery of xylitol it is possible to avoid the accumulation of sorbitol caused by recycling by either carrying out the fractionation initially on a resin of either $Al^{+++}$ or $Fe^{+++}$ form or by using a double fractionation process where a first fractionation is conducted on a resin in alkaline earth metal form followed by a second fractionation on a resin in $Al^{+++}$ or $Fe^{+++}$ form. The most advantageous method is usually to divide the solution into two parallel streams and carry out the fractionations on two parallel columns one of which is $Al^{+++}$-form and the other in $Sr^{++}$-form.

In accordance with the method of the present invention, the crude xylitol crystallization step is conducted by subjecting the mixed polyol solution to a crystallization procedure. The solution is concentrated to a water content within the range of 87 to 94% by weight, preferably 90–92%. The temperature of the material is then adjusted to below the saturation temperature of xylitol, e.g. 55°–75° C. The solution is then seeded with xylitol crystals and cooled according to an empirical program to a temperature of 25°–40° C. The seed crystals preferably have a size within the range of 2 to 20μ and are added in the amount of 0.02–0.1%. Preferably, about 70% of the xylitol in the solution is removed by this procedure as crude xylitol crystals. However, good results are obtained where from 60 to 75% of the xylitol is removed in the crude crystallization step.

Washing of the crystals in the centrifuge basket is not necessary, but is often used in order to improve the purification effect. The crystals obtained by the crude crystallization may next be washed with a small amount of water, preferably about 2% by weight of the crystals, in a basket-type centrifuge to remove the major portion of the microcrystals of galactitol adhering to the xylitol crystals. The microcrystals of galactitol co-crystallize with xylitol during the crystallization procedure. The washing solution is combined with the mother liquor and set aside for further processing. The crude xylitol crystals are redissolved in water and subjected again to a recrystallization to provide crystals of xylitol containing less than 0.2% galactitol and over 99.5% xylitol.

The recrystallization may be carried out either by evaporation of the saturated solution or by cooling the saturated solution in order to cause supersaturation of the solution.

If the recrystallization is carried out by evaporation, a vacuum crystallizer of the type which is used in the sucrose industry is suitable. The xylitol solution which contains 92–100% xylitol of d.s. is heated to 60°–65° C in vacuum and evaporated to 87–91% d.s. content. The solution is seeded and the crystals are caused to grow by maintaining the supersaturation. By this method about 65% of the xylitol which is present in the solution is recovered as pure xylitol crystals. The crystals are separated from the mother liquor by centrifuging.

Another equally advantageous method to carry out the recrystallization is as follows:

The xylitol solution which contains 92–100% xylitol on d.s. is evaporated to 85–91% d.s. (preferably 88%) and heated to 55°–65° C (preferably 60° C). The solution is seeded and cooled as described above for the crude crystallization. The end temperature is 25°–40° C. By this method 60–65% of the xylitol is recovered as pure xylitol crystals. The crystals are separated from the mother liquor by centrifuging. The liquid removed by centrifuging and the washing liquid may be supplied to the reserved mother liquor and washings from the crude crystallization procedure. Alternatively, the mother liquor from the recrystallization step together with washing liquids, if any, may be returned to the system by combining them with the feed of mixed polyols just prior to the crude crystallization step.

The mother liquor and washing solutions from the crude crystallization are treated to recover a major portion of the xylitol remaining therein. The solution is subjected to a purification procedure which first removes a major portion of the galactitol in the form of microcrystals, and thereafter fractionates the reserved liquids by passing them through one or more chromatographic ion-exchange columns.

Before subjecting the combined mother liquor and washed liquids to separation on the chromatographic columns of ion-exchange resin, it is usually advantageous to remove from the solution, by centrifugation, sedimentation, or filtration, the microcrystals of galactitol which form during the crude xylitol crystallization step. These microcrystals are so small that they are washed from the xylitol crystals together with the mother liquor during the step of washing the crude xylitol crystals.

It has previously been found that polyols are fractionated differently and eluted in different order from columns which contain resins in the alkaline earth form on one hand, and the $Al^{+++}$ or $Fe^{+++}$ form on the other hand. If two columns which are filled with resins in the different cationic forms work in parallel, it is possible to obtain a combined xylitol-rich fraction in which the galactitol and mannitol content, as well as the sorbitol content, is acceptably low. A column in alkaline earth form effectively removes most of the other polyols including the arabinitol and mannitol, while a column in the $Al^{+++}$ or $Fe^{+++}$ form can remove the major part of the sorbitol. By supplying approximately equal quantities of feed solution to each type of column in parallel, and by combining the eluates from the two columns, a xylitol solution of acceptable purity for subsequent further crystallization is obtained.

Where columns of these two types are combined in series, purification is more effective, but the eluted solutions are more dilute, which means an increased cost due to evaporation requirements. It has been found that a parallel purification system is usually more advantageous; however, this depends upon the composition of the mixed polyols used as the raw material and in some applications, a combination of the columns in series will lead to more economical results.

Following the fractionation procedure, the xylitol-rich fraction obtained thereby is returned to the crude crystallization step. The intermediate fractions are returned to be passed again through the fractionation step and the remaining impure fractions are combined to form a mixed polyol by-product which can be discarded or preferably is used as an animal feed or source of carbohydrates in industrial fermentations.

The method of the present invention makes it possible to recover from 96-98% of the xylitol present in the original mixed polyol solution as a pharmaceutical grade crystalline xylitol. The purity of the xylitol crystals is over 99.5%, and its galactitol content is less than 0.2%.

DESCRIPTION OF THE DRAWINGS

The invention will be further described with reference to the attached drawings, in which.

Figure 1:
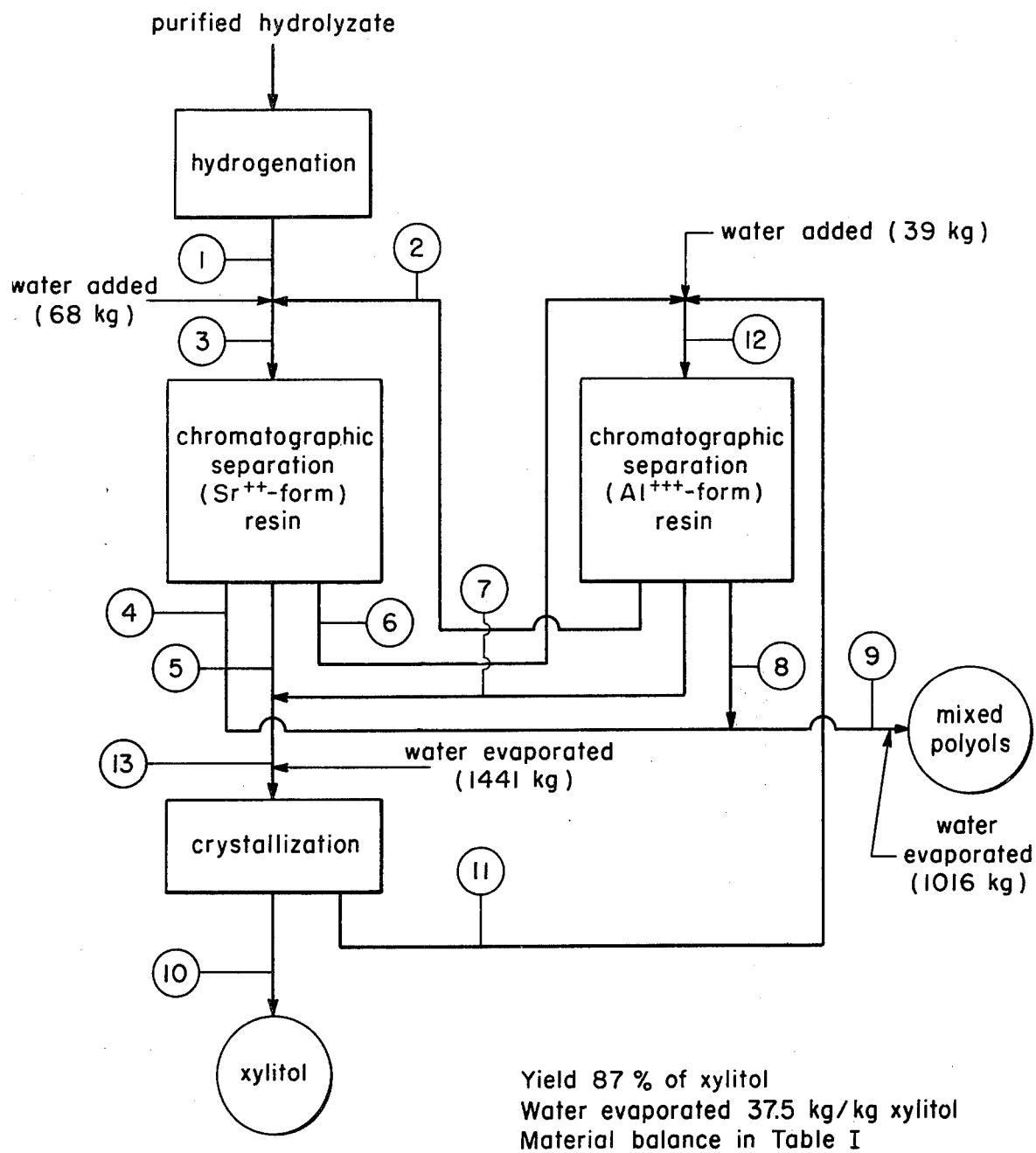
FIG. 1 is a flow diagram showing generally the process of the prior art.

The flow diagram of a prior art method for the preparation of xylitol from polyol solutions shown in FIG. 1 identifies sampling points 1 through 13. A corresponding analysis of material from each sampling point is shown in Table I below.

in xylitol and high in other polyols including mannitol and arabinitol. This fraction is removed from the system as a mixed polyol by-product at 9.

The middle fraction, sample point 6, from the first fractionation, is combined with the mother liquor, 11, from the crystallization, and the combined streams are fractionated on a resin column in $Al^{+++}$-form in order to recover a xylitol-rich fraction, sample point 7 from which additional xylitol can be crystallized.

Fraction 13 contains 88% xylitol, and while it is relatively high in sorbitol, it is low in most of the other polyols. Fraction 8 which is low in xylitol and high in other polyols is combined with stream 4 and removed from the system as a mixed polyol by-product at 9. Fraction 2, which is high in xylitol, is returned for mixture with the incoming stream of raw material, and recycled through the first chromatographic column containing resin in $Sr^{++}$-form.

According to the prior art method described above, it is possible to recover 87% of the xylitol in the raw feed solution as a pharmaceutical grade product. However, the solutions which are eluted from the fractionation columns are rather dilute and thus cause increased evaporation costs. The total amount of water which must be evaporated for each kg of xylitol recovered is 36-38 kg water.

According to the improved method of the present invention, a major part of the xylitol is removed from solution by the crude crystallization and recrystallization steps. In addition, the main part of the galactitol is removed by centrifugation or sedimentation from the mother liquor of the crude crystallization. The amount of remaining impurities is significantly decreased in the mother liquor by fractionation on parallel ion-exchange columns. By this method the amount of water which is added to the process and which must be removed by evaporation is decreased. Furthermore, the investment costs for equipment are decreased, for although there is

TABLE I

| | Example of material balance for prior art method for xylitol production shown in FIG. 1 | | | | | | | | | | | | | |
|---|---|---|---|---|---|---|---|---|---|---|---|---|---|---|
| | concentr. | total ds. | H$_2$O | composition (kg) | | | | | | composition % | | | | |
| No | g/100 g | kg | kg | xy | ar | ga | so | ma | others | xy | ar | ga | so | ma | others |
| 1 | 50 | 100 | 100 | 76 | 5.5 | 4.0 | 5.5 | 6.5 | 2.5 | 76 | 5.5 | 4.0 | 5.5 | 6.5 | 2.5 |
| 2 | 8.0 | 18 | 205 | 13 | 0.8 | 1.1 | 2.5 | 0.2 | 0.3 | 73 | 4.3 | 5.9 | 14 | 1.3 | 1.8 |
| 3 | 24 | 118 | 373 | 89 | 6.3 | 5.0 | 8.0 | 6.7 | 2.8 | 76 | 5.3 | 4.3 | 6.8 | 5.7 | 2.4 |
| 4 | 3.9 | 22 | 534 | 6.0 | 5.0 | 2.0 | 0.7 | 5.9 | 2.1 | 28 | 23 | 9.3 | 3.1 | 27 | 9.7 |
| 5 | 8.5 | 68 | 732 | 61 | 0.2 | 1.1 | 5.4 | 0.1 | 0.2 | 90 | 0.3 | 1.7 | 7.9 | 0.1 | 0.3 |
| 6 | 13 | 28 | 188 | 22 | 1.0 | 1.9 | 1.9 | 0.7 | 0.5 | 78 | 3.7 | 6.7 | 6.8 | 2.6 | 1.9 |
| 7 | 6.0 | 46 | 722 | 40 | 1.7 | 1.0 | 2.3 | 0.2 | 1.1 | 87 | 3.7 | 2.1 | 5.1 | 0.4 | 2.3 |
| 8 | 2.5 | 13 | 500 | 4.5 | 0.5 | 2.0 | 4.8 | 0.6 | 0.4 | 35 | 3.9 | 15 | 38 | 4.5 | 3.2 |
| 9 | 3.2 - 65 | 34 | 1034 | 10 | 5.5 | 4.0 | 5.5 | 6.5 | 2.5 | 30 | 16 | 12 | 16 | 19 | 7.3 |
| 10 | 100 | 66 | — | — | — | — | — | — | — | 100 | — | — | — | — | — |
| 11 | 75 | 49 | 16 | 35 | 1.9 | 2.1 | 7.8 | 0.3 | 1.3 | 73 | 4.0 | 4.3 | 16 | 0.5 | 2.6 |
| 12 | 24 | 77 | 243 | 57 | 3.0 | 4.0 | 10 | 1.0 | 1.8 | 75 | 3.9 | 5.2 | 13 | 1.3 | 2.3 |
| 13 | 73 - 90 | 114 | 13 | 101 | 1.9 | 2.1 | 7.7 | 0.3 | 1.3 | 88 | 1.7 | 1.8 | 6.8 | 0.2 | 1.1 |

The numbers in lefthand column refer to sampling points in FIG. 1
ds. = dry substance
xy = xylitol
ar = arabinitol
ga = galactitol
so = sorbitol
ma = mannitol According to the prior art method, the impure polyol solution having the composition given for point No. 3 in Table I, including 76% xylitol, is chromatographically fractionated on a column of ion-exchange resin, cross-coupled with 3.5% divinyl benzene in $Sr^{++}$-form, and three fractions are recovered. The last fraction through the column, sample point No. 5, contains 90% xylitol, is relatively high in sorbitol but is low in the other polyols. This fraction is carried to the crystallization step. The first fraction through the column, sample point 4, is low an increased crystallizer capacity required, there is simultaneously a decreased need for fractionation capacity.

The method of the present invention is further described below in detail in the working Examples.

EXAMPLE 1

A xylose-rich birch wood hemicellulose hydrolysate was neutralized and purified by conventional ion-exclusion and decolorization. The purified hydrolysate had the following composition:

| Xylose | 76% of total sugars |
|---|---|
| arabinose | 5% |
| mannose | 7% |
| galactose | 4% |
| glucose | 6% |
| others | 2% |

The purified hydrolysate was hydrogenated by Raney-nickel catalyst. The temperature was 130° C and the hydrogen pressure 40 kg/m². The composition of the hydrogenated solution is shown in Table 2, sample point No. 1.

From the hydrogenated solution crude xylitol was crystallized by evaporating the solution to 92% (weight d.s. content) at 65° C. The solution was seeded with 0.02% by weight of xylitol crystals and cooled to 35° C. The crystallization was carried out in a conventional crystallizer which was equipped with a mixing device. Seventy percent of the xylitol present in the solution crystallized as crude crystals which were separated from the mother liquor in a basket centrifuge. The xylitol crystals are separated from the mother liquor in a basket-type centrifuge. The apparatus used here and hereinafter in the working examples of the application, unless otherwise specified, is a Variable-Speed Batch Automatic Centrifugal Filter, of the type described in the Chemical Engineering Deskbook, Feb. 15, 1971, page 55.

The purity of the crystals was 94%, and they contained 0.8% galactitol, and about 5% other polyols. The crude crystals were dissolved in water to a 60% weight solution and recrystallized. The solution contained 94% xylitol on d.s. and was evaporated to 88% dry substance content. The temperature at the beginning of the crystallization was 60° C. The solution was seeded with 0.02% seed crystals and cooled to 30° C. The crystallization was carried out in a conventional crystallizer which was equipped with a mixer. The crystals were separated by centrifuging and 65% of the xylitol was recovered as pure crystals.

Analysis of the xylitol after drying of the crystals:

| Water (Karl Fischer method) | 0.07 % | |
|---|---|---|
| Ash (conductivity) | 0.001% | |
| Xylitol | 99.9% | (GLC analysis) |
| Sorbitol | 0.1% | |
| Galactitol | 0.0% | |
| Mannitol | 0.0% | |
| Arabinitol | 0.0% | |

The purity of the pure crystals was over 99.5% and they contained less than 0.2% galactitol.

In the crude crystallization, the main part of the galactitol which was present in the solution crystallized in the form of microcrystals which were washed through the centrifugal basket and remained in the mother liquor. The galactitol microcrystals were separated from the syrup by centrifuging in a sedimentation centrifuge, an Alfa-Laval solids-ejecting separator, of the type described as a chemical industry model BRPX 309S, sold by Alfa-Laval DeLaval Group, Sweden. The syrup was then divided into two parts and fractionated on two parallel columns which were filled with polystyrene sulfonate resin cross-coupled with di-vinyl benzene. One of the columns was filled with resin in Al+++ -form and the other with resin in Sr++ -form.

Figure 2:
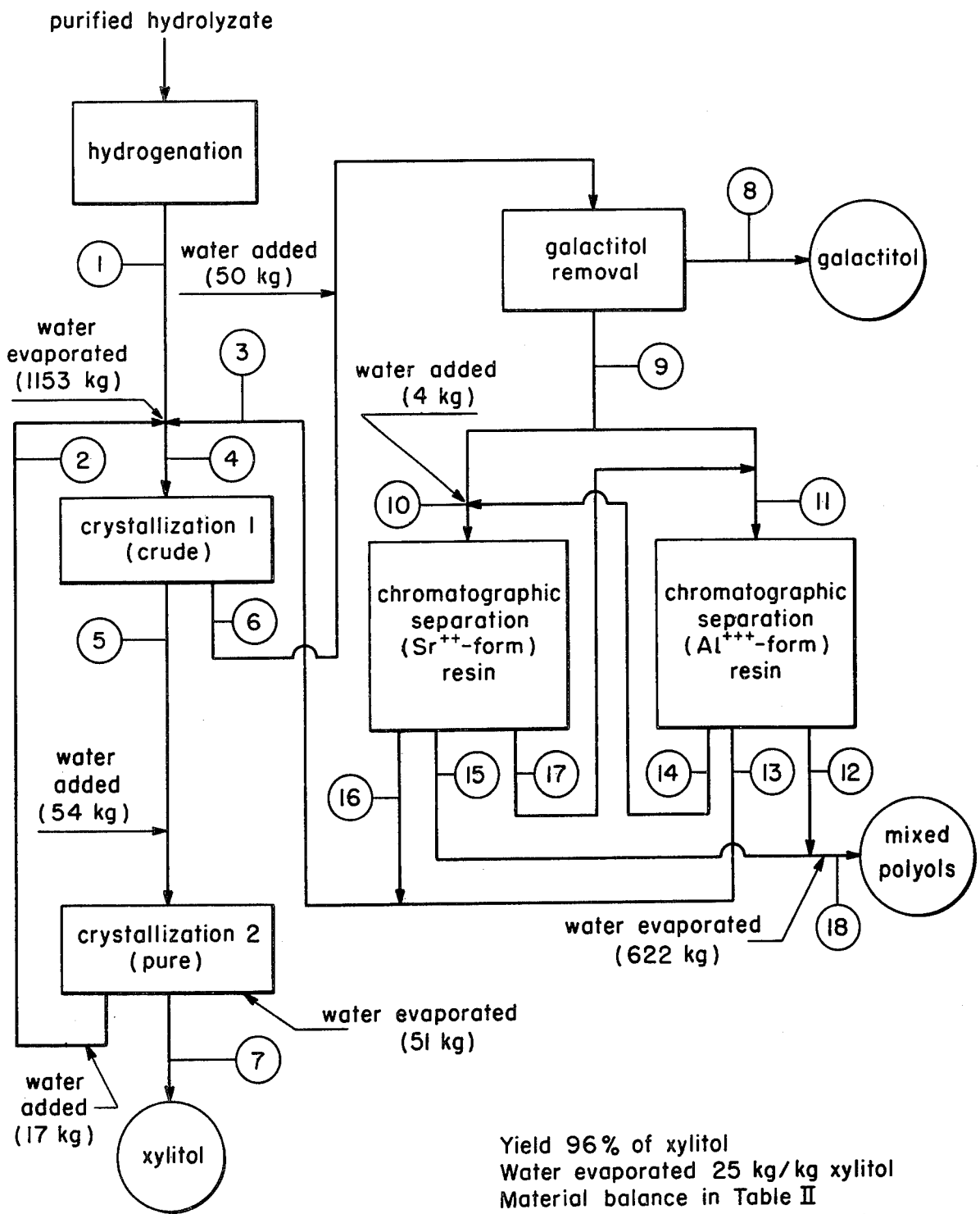
FIG. 2 is a flow diagram showing one preferred embodiment of the present invention.

The process of this example was carried out as shown in the flow diagram of FIG. 2 of the attached drawings. An analysis of material from each sampling identified in FIG. 2 is given by corresponding number in Table 2 below. Referring to FIG. 2, a purified hydrolysate, 1, after hydrogenation, is combined with mother liquor, 2, from the recrystallization stage, crystallization 2, and xylitol-rich return fractions 3, to form a feed for the crude crystallization 1. Fractionation of the mother liquor and washing liquids followed galactitol removal, stream 9 was divided into two parallel streams 10 and 11. From both columns the xylitol-rich fractions were combined and recirculated to the crude crystallization, 3. The return fractions, 17 and 14, were fed to opposite columns (cross-return) and the remaining impure fractions were combined to a mixed polyol by-product which was removed from the system.

The yield of pure xylitol was 96% of the xylitol present in the hydrogenated solution.

TABLE 2

Material balance for xylitol production by double crystallizaton combined with removal of microcrystalline galactitol and syrups fractionation

| | concentr. | total | H₂O | composition (kg) | | | | | | composition % | | | | | |
|---|---|---|---|---|---|---|---|---|---|---|---|---|---|---|---|
| No | g/100 g | d.s. kg | kg | xy | ar | ga | so | ma | others | xy | ar | ga | so | ma | others |
| 1 | 50 | 100 | 100 | 76 | 5.5 | 4.0 | 5.5 | 6.5 | 2.5 | 76 | 5.5 | 4.0 | 5.5 | 6.5 | 2.5 |
| 2 | 70 | 53 | 23 | 45 | 2.0 | 1.0 | 2.7 | 1.6 | 0.6 | 85 | 3.8 | 1.9 | 5.1 | 3.0 | 1.1 |
| 3 | 6.6 | 74 | 1051 | 48 | 4.7 | 1.4 | 16.5 | 0.9 | 2.9 | 64.5 | 6.3 | 1.9 | 22 | 1.2 | 3.9 |
| 4 | 92 | 227 | 21 | 169 | 12 | 6.4 | 25 | 9.0 | 6.0 | 74 | 5.4 | 2.8 | 11 | 4.0 | 2.6 |
| 5 | 100 – 70 | 126 | 2 | 118 | 2.0 | 1.0 | 2.7 | 1.6 | 0.6 | 94 | 1.6 | 0.8 | 2.1 | 1.3 | 0.5 |
| 6 | 84 – 60 | 101 | 19 | 51 | 10 | 5.4 | 22 | 7.4 | 5.4 | 50 | 10 | 5.3 | 22 | 7.3 | 5.3 |
| 7 | 100 | 73 | — | 73 | — | — | — | — | — | 100 | — | — | — | — | — |
| 8 | 65 | 4.1 | 2 | 1.0 | 0.2 | 2.2 | 0.5 | 0.2 | — | 24 | 4.9 | 54 | 12 | 4.9 | — |
| 9 | 59 | 97 | 67 | 50 | 10 | 3.2 | 21.5 | 7.2 | 5.4 | 51 | 10 | 3.3 | 22 | 7.4 | 5.5 |
| 10 | 28 | 64 | 94 | 31.5 | 7.0 | 2.3 | 15 | 4.9 | 3.6 | 49 | 11 | 3.6 | 23 | 7.6 | 5.6 |
| 11 | 18 | 52 | 242 | 24.5 | 7.1 | 2.5 | 10.5 | 4.3 | 3.5 | 47 | 13.5 | 4.8 | 20 | 8.2 | 6.7 |
| 12 | 3.3 | 14 | 418 | 1.8 | 1.9 | 1.6 | 4.9 | 3.1 | 0.6 | 13 | 14 | 11.5 | 35 | 22 | 4.3 |
| 13 | 6.2 | 33 | 496 | 21 | 4.2 | 0.5 | 3.9 | 0.7 | 2.5 | 64 | 13 | 1.5 | 12 | 2.1 | 7.6 |
| 14 | 9.5 | 5.6 | 53 | 1.7 | 1.0 | 0.4 | 1.7 | 0.5 | 0.3 | 30 | 18 | 7.1 | 30 | 8.9 | 5.4 |
| 15 | 4.0 | 9.0 | 216 | 0.2 | 3.4 | 0.2 | 0.1 | 3.2 | 1.9 | 2.2 | 38 | 2.2 | 1.1 | 36 | 21 |
| 16 | 7.0 | 42 | 553 | 27 | 0.5 | 0.9 | 13 | 0.2 | 0.4 | 65 | 1.2 | 2.2 | 30 | 0.5 | 1.0 |
| 17 | 6.0 | 13.5 | 212 | 4.3 | 3.1 | 1.2 | 2.1 | 1.5 | 1.3 | 32 | 23 | 8.8 | 16 | 11 | 9.6 |
| 18 | 3.5 – 65 | 23 | 634 | 2.0 | 5.3 | 1.9 | 5.0 | 6.3 | 2.5 | 8.7 | 23 | 8.3 | 22 | 27 | 11 |

The numbers refer to sample points in FIG. 2
d.s. = dry substance
xy = xylitol
ar = arabinitol
ga = galactitol
so = sorbitol
ma = mannitol

EXAMPLE 2

A purified hemicellulose hydrolysate was hydrogenated as in Example 1. From the solution, crude xylitol was crystallized, the crystals dissolved and pure xylitol recovered as in Example 1. From the mother liquor the galactitol was removed as in Example 1. The syrup was then subjected to fractionation on two parallel columns which were similar as those of Example 1. The xylitol-rich fractions, 13 and 16, from both columns were combined and recirculated to the crude crystallization. The return fractions, 14 and 17, from both columns were combined and returned to the syrup from which galactitol was removed. The remaining impure fractions were combined to a mixed polyol by-product, which was removed from the system.

Figure 3:
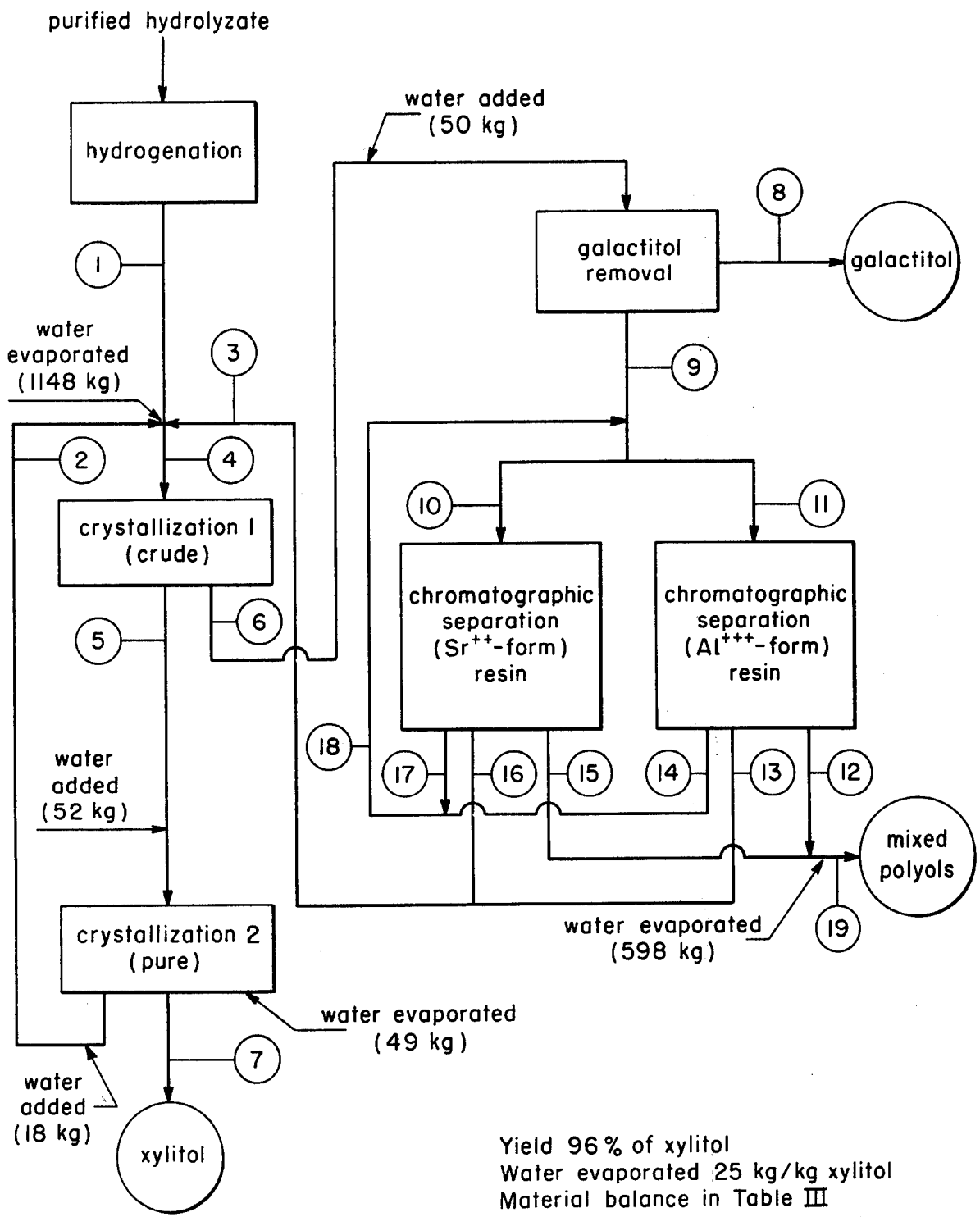
FIG. 3 is a flow diagram showing an alternative preferred embodiment of the present invention.

The method is illustrated in FIG. 3. A corresponding material balance is shown in Table 3 below.

The yield of pure xylitol was 96%. The pure crystals contained over 99.5% xylitol and less than 0.2% galactitol.

supplied to the column as a 25 g/100 g water solution. The feed solution had the following composition:

| | |
|---|---|
| Xylitol | 52% |
| Arabinitol | 10% |
| Galactitol | 7% |
| Sorbitol | 14% |
| Mannitol | 13% |
| Others | 4% |

Figure 5:
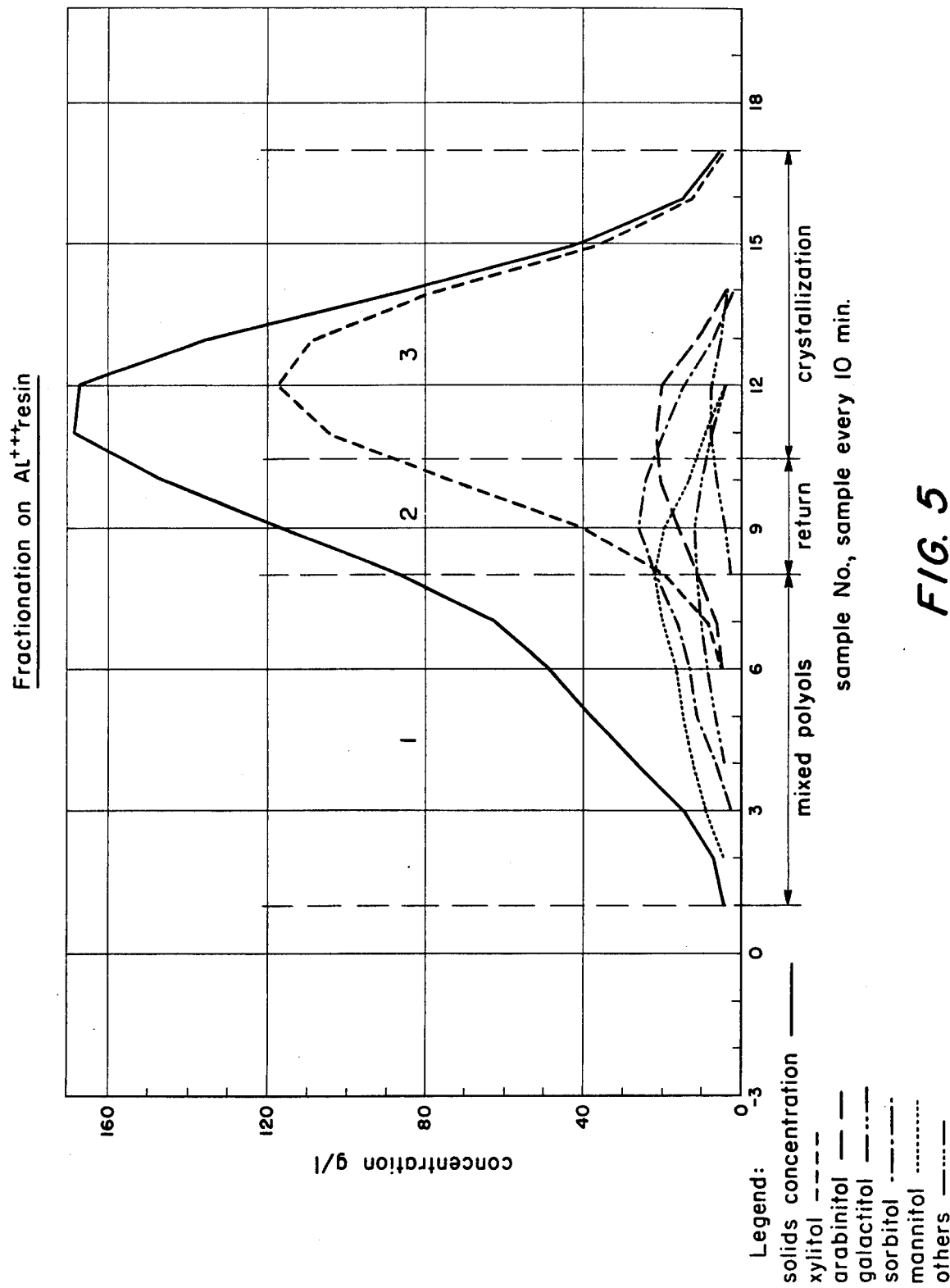
FIG. 5 is a graph showing the fractionation of a mixture of polyols on a column of resins in $Al^{+++}$ form.

Elution was carried out with water. The polyols were separated in accordance with the curves shown in FIG. 5. Three fractions were collected. The first fraction, which covered the first 70 minutes of operation, was a mixed polyol by-product or waste fraction, which was collected and separated from the system. The second fraction was the return fraction, and covered the next 25 minutes of separation of the column. This material was returned to an earlier point in the process, e.g. combined with the mother liquor from next crude crystallization. The third fraction identified as the crystallization or product fraction was obtained during the last

TABLE 3

Material balance for xylitol production by double crystallization combined with removal of microcrystalline galactitol and syrups fractionation

| No | concentr. g/100 g | total d.s. kg | H₂O kg | composition (kg) | | | | | | composition % | | | | | |
|---|---|---|---|---|---|---|---|---|---|---|---|---|---|---|---|
| | | | | xy | ar | ga | so | ma | others | xy | ar | ga | so | ma | others |
| 1 | 50 | 100 | 100 | 76 | 5.5 | 4.0 | 5.5 | 6.5 | 2.5 | 76 | 5.5 | 4.0 | 5.5 | 6.5 | 2.5 |
| 2 | 70 | 53 | 23 | 45 | 1.8 | 1.1 | 2.9 | 1.6 | 0.5 | 85 | 3.4 | 2.1 | 5.5 | 3.0 | 0.9 |
| 3 | 6.7 | 75 | 1047 | 48 | 3.8 | 1.7 | 18 | 0.8 | 2.3 | 64 | 5.1 | 2.3 | 24 | 1.1 | 3.1 |
| 4 | 92 | 227 | 22 | 169 | 11 | 6.7 | 26 | 8.9 | 5.4 | 74 | 4.8 | 3.0 | 11.5 | 3.9 | 2.4 |
| 5 | −70 | 126 | 2 − 54 | 118 | 1.8 | 1.1 | 2.9 | 1.6 | 0.5 | 94 | 1.4 | 0.9 | 2.3 | 1.3 | 0.4 |
| 6 | 84 − 60 | 102 | 20 − 70 | 51 | 9.3 | 5.7 | 23.5 | 7.3 | 4.8 | 50 | 9.2 | 5.6 | 23 | 7.2 | 4.7 |
| 7 | 100 | 73 | — | 73 | — | — | — | — | — | 100 | — | — | — | — | — |
| 8 | 65 | 4.2 | 2.0 | 1.0 | 0.2 | 2.3 | 0.5 | 0.2 | — | 24 | 4.8 | 55 | 12 | 4.8 | — |
| 9 | 59 | 97 | 68 | 50 | 9.1 | 3.4 | 23 | 7.1 | 4.8 | 51 | 9.3 | 3.5 | 24 | 7.3 | 4.9 |
| 10 | 25 | 72 | 226 | 35 | 8.1 | 3.3 | 16 | 5.2 | 3.9 | 49 | 11 | 4.6 | 23 | 7.2 | 5.4 |
| 11 | 25 | 47 | 149 | 23 | 5.4 | 2.2 | 11 | 3.4 | 2.6 | 49 | 11 | 4.7 | 23 | 7.2 | 5.5 |
| 12 | 3.3 | 12 | 346 | 1.8 | 1.5 | 1.5 | 4.9 | 1.7 | 0.4 | 15 | 13 | 13 | 41.5 | 14 | 3.4 |
| 13 | 6.2 | 30 | 458 | 19 | 3.2 | 0.4 | 4.8 | 0.6 | 1.9 | 64 | 11 | 1.3 | 16 | 2.0 | 6.3 |
| 14 | 9.5 | 5.1 | 49 | 1.8 | 0.7 | 0.3 | 1.7 | 0.3 | 0.3 | 35 | 14 | 5.9 | 33 | 5.9 | 5.9 |
| 15 | 4.0 | 11 | 264 | 0.2 | 3.8 | 0.2 | 0.1 | 4.6 | 2.1 | 1.8 | 34.5 | 1.8 | 0.9 | 42 | 19 |
| 16 | 7.0 | 44 | 589 | 29 | 0.6 | 1.3 | 13 | 0.2 | 0.4 | 65 | 1.4 | 29 | 30 | 0.5 | 0.9 |
| 17 | 6.0 | 17 | 258 | 6.2 | 3.7 | 1.8 | 2.3 | 1.2 | 1.4 | 37 | 22 | 11 | 14 | 7.2 | 8.4 |
| 18 | 6.6 | 22 | 307 | 8.0 | 4.4 | 2.1 | 4.0 | 1.5 | 1.7 | 37 | 20 | 9.7 | 18 | 6.9 | 7.8 |
| 19 | 3.6 − 65 | 23 | 610 − 12 | 2.0 | 5.3 | 1.7 | 5.0 | 6.3 | 2.5 | 8.8 | 23 | 7.5 | 22 | 28 | 11 |

The numbers refer to sample points in FIG. 3
d.s. = dry substance
xy = xylitol
ar = arabinitol
ga = galactitol
so = sorbitol
ma = mannitol Examples 3 and 4 illustrate further the separation step on columns in Al+++ and Sr++ -form, respectively.

EXAMPLE 3

A purified hemicellulose hydrolysate was hydrogenated as in Example 1. From the solution, crude xylitol was crystallized, the crystals dissolved, and pure xylitol recrystallized and recovered as in Example 1. The mother liquor from the crude crystallization was combined with the washing liquids and the solution was separated on a column in Al+++ -form.

The combined mother liquor and washing liquids were then subjected to a fractionation step by feeding it to a column of sulfonated polystyrene resin cross-coupled with 3-4% di-vinyl benzene, the resin being in the Al+++ form. The resin was contained in a pilot plant column having a diameter of 22.5 cm. The temperature was 55° C. The resin had a mean particle size of 0.36 mm and the column had a height of 5 meters. The material was evenly fed to the top of the column at a rate of 0.0148 m³/h. In this manner, 3 kg of dry substance was 65 minutes of column operation and contained a high level of xylitol and a relatively low level of sorbitol as shown in the Figure. This fraction was combined with the stream of xylitol solution going to the recrystallization step, as described earlier in Examples 1 and 2.

The following table summarizes the characteristics of the three fractions:

Distribution of sugars into the 3 fractions (% of total amount) was as follows:

| | Product Frac. | Return Frac. | Waste Frac. |
|---|---|---|---|
| Xylitol | 91% | 6% | 3% |
| arabinitol | 73% | 14% | 13% |
| galactitol | 40% | 21% | 39% |
| sorbitol | 50% | 20% | 30% |
| mannitol | 28% | 21% | 51% |
| others | 82% | 9% | 9% |

Composition of the fractions (% of dry substance) was as follows:

|  | Product Fract. | Return Fract. | Waste Fract. |
|---|---|---|---|
| Xylitol | 67% | 25 % | 19.5% |
| arabinitol | 10% | 12.5% | 8 % |
| galactitol | 4% | 12.5% | 16 % |
| sorbitol | 10% | 24 % | 25.5% |
| mannitol | 5% | 23 % | 39 % |
| others | 4% | 3 % | 2 % |

Total concentration of the fractions (g/1000 ml)

| Product Fract. | Return Fract. | Waste Fract. |
|---|---|---|
| 102 g/l | 90 g/l | 26 g/l |

EXAMPLE 4

A purified hemicellulose hydrolysate was hydrogenated as in Example 1. From the solution, crude xylitol was crystallized, the crystals dissolved, and pure xylitol recrystallized and recovered as in Example 1.

The mother liquor from the crude crystallization was combined with the washing liquids, and the combined liquids were then subjected to a fractionation step by feeding it to a column of sulfonated polystyrene resin cross-coupled with 3–4% di-vinyl benzene, the resin being in the $Sr^{++}$ form. The resin was contained in a pilot plant column having a diameter of 22.5 cm. The temperature was 55° C. The resin had a mean particle size of 0.4 mm and the column had a height of 3.5 m. The material was fed to the top of the column at a feed rate of 0.0279 m$^3$/h. In this rate, 3 kg of dry substance was supplied to the column as a 23 g/100 g water solution. The feed had the following composition:

| Xylitol | 51% |
|---|---|
| Arabinitol | 13% |
| Galactitol | 5% |
| Sorbitol | 12% |
| Mannitol | 13% |
| Others | 6% |

Figure 4:
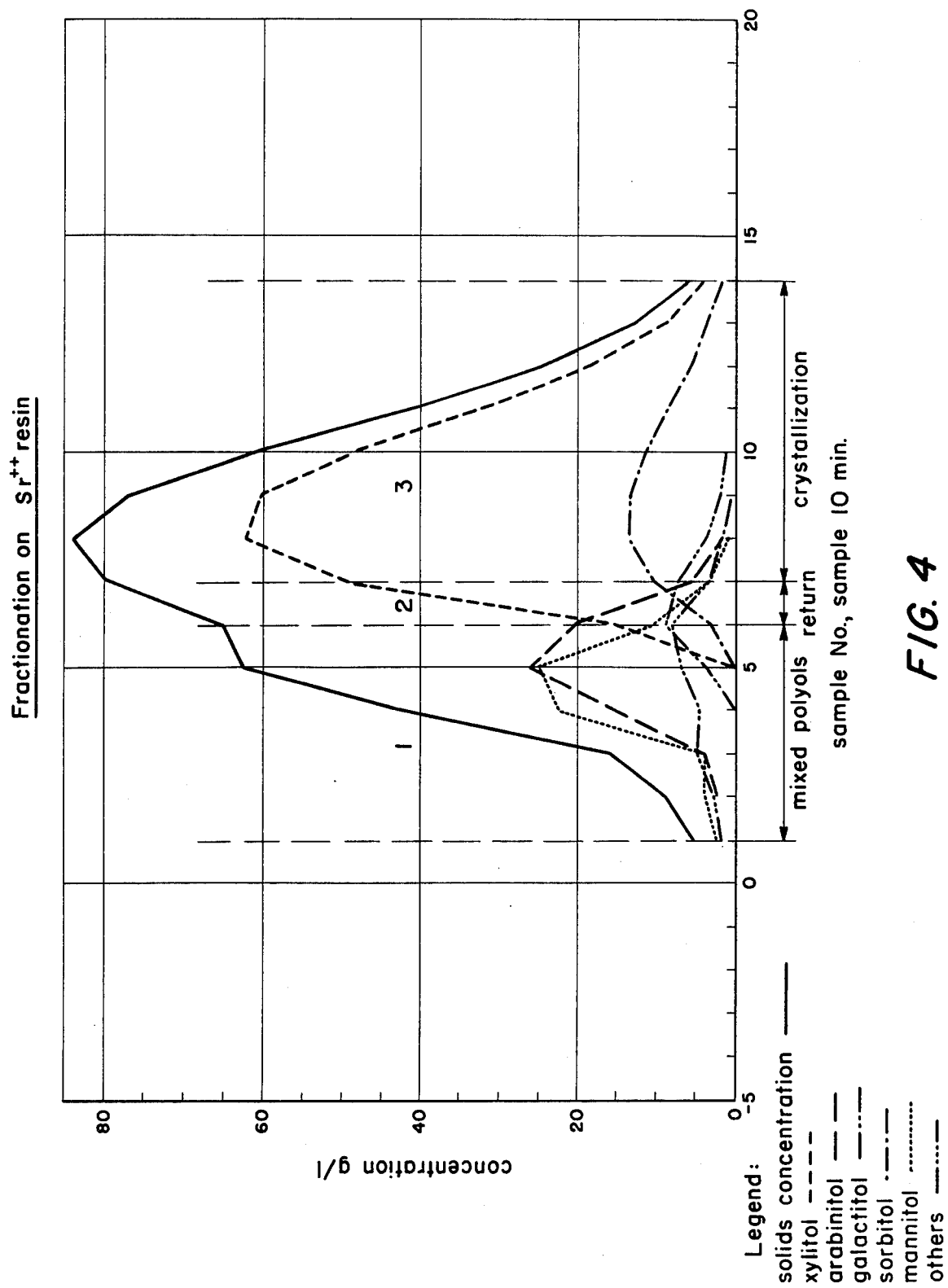
FIG. 4 is a graph showing the course of fractionation of a polyol mixture on a resin in $Sr^{++}$ form.

Elution was carried out with water. The polyols were separated as shown in FIG. 4. Three fractions were collected. The first fraction, which covered the first 50 minutes of operation, was a mixed polyol by-product or waste fraction which was collected and separated from the system. The second or return fraction covered the next 10 minutes of operation of the column, and this material was returned to an earlier point in the process, e.g. combined with the mother liquor from the next crude crystallization. The third fraction, termed the product fraction, covering the last 70 minutes, contained a high level of xylitol and a relatively low level of sorbitol as shown in the Figure. This fraction was combined with the stream of xylitol solution going to the recrystallization step, as described earlier in Examples 1 and 2.

The following table summarizes the characteristics of the three fractions:

Distribution of sugars into the 3 fractions (% of total amount) was as follows:

|  | Product Fract. | Return Fract. | Waste Fract. |
|---|---|---|---|
| Xylitol | 84.5% | 15 % | 0.5% |
| arabinitol | 7 % | 43 % | 50 % |
| galactitol | 38.5% | 51.5% | 10 % |
| sorbitol | 87 % | 13 % | < 0.5% |
| mannitol | 3.5% | 29.5% | 67 % |
| others | 11 % | 36 % | 53 % |

Composition of the fractions (% of dry substance) was as follows:

|  | Product Fract. | Return Fract. | Waste Fract. |
|---|---|---|---|
| Xylitol | 75% | 33% | 1.5% |
| arabinitol | 2% | 25% | 35 % |
| galactitol | 3% | 10% | 2.5% |
| sorbitol | 18% | 7% | < 0.5% |
| mannitol | 1% | 4% | 45 % |
| others | 1% | 1% | 16 % |

Total concentration of the fractions (g/1000 ml)

| Product Fract. | Return Fract. | Waste Fract. |
|---|---|---|
| 49 g/l | 69 g/l | 22 g/l |

From the Examples 3 and 4 it is evident that the two different columns separate the polyols differently. This difference is used in the process of this invention to improve the purification and increase the yield. It is advantageous to divide the liquors which are to be separated into two parallel streams one of which is fed to a column in $Al^{+++}$-form and the other to a column in $Sr^{++}$-form. The separation effect is of course better if the columns are in series. But the parallel method is more advantageous because of less dilution of the solutions.

We claim:

1. A method for obtaining xylitol crystals of pharmaceutical grade from an aqueous solution of a mixture of polyols including xylitol which comprises the steps of
    a. subjecting said solution to a crude xylitol crystallization step to crystallize a major portion of the xylitol therein while leaving a mother liquor,
    b. removing the crude crystals from the mother liquor,
    c. recrystallizing the xylitol by dissolving the crude crystals in water and crystallizing them to provide crystals of high purity, while leaving a mother liquor, and
    d. recovering residual xylitol from the mother liquors from the crystallization and recrystallization steps by subjecting at least a portion of the mother liquors to a chromatographic fractionation using at least two columns containing sulfonated polystyrene cation exchange resins cross-coupled with di-vinyl benzene, one of said columns containing the resin in an alkaline earth form and the other of said columns containing the resin in an $Al^{+++}$ or $Fe^{+++}$ form.

2. The method of claim 1, wherein the at least two chromatographic columns are arranged in series, and the feed solutions undergoing fractionation pass through first one of the columns and then the other.

3. A method for obtaining xylitol crystals of pharmaceutical grade from an aqueous solution of a mixture of polyols including xylitol which comprises the steps of
    a. subjecting said solution to a crude xylitol crystallization step to crystallize a major portion of the xylitol therein while leaving a mother liquor,
    b. removing the crude crystals from the mother liquor,
    c. purifying the crude crystals by washing the crystals to remove microcrystals of galactitol formed during the xylitol crystallization steps from their surfaces,
    d. recovering microcrystals of galactitol by combining the washing liquid and the crystallization mother liquor and subjecting it to a galactitol removal step whereby the microcrystals of galactitol are recovered from the said combined liquids, and e. recovering residual xylitol from the liquids in step (d) by subjecting at least a portion of the liquids to chromatographic fractionation.

4. The method of claim 1, wherein the at least two chromatographic columns are arranged in parallel, and the feed solution is divided, one portion passing through one of said columns and the other portion passing through the other of said columns, the desired fractions from each of said columns being combined after fractionation.

5. A method for obtaining xylitol crystals of pharmaceutical grade having less than about −0.2% by weight of galactitol, which comprises
   a. preparing a pentose-rich hemicellulose hydrolysate,
   b. purifying the hydrolysate by removing suspended solids, inorganic salts, and a major portion of organic impurities and color therefrom,
   c. hydrogenating the purified hydrolysate to form a mixed polyol solution containing from 60–85% xylitol on a dry solids basis,
   d. subjecting said mixed polyol solution to a crude xylitol crystallization step to crystallize a major portion of the xylitol therein while leaving a mother liquor,
   e. removing the crude xylitol crystals from the mother liquor,
   f. recrystallizing the xylitol by dissolving the crude crystals in water and recrystallizing the xylitol to provide crystals of high purity,
   g. separating the crystals from the mother liquor, and
   h. recovering residual xylitol from the mother liquor obtained in step (d) by
      i. removing galactitol crystals from the mother liquor,
      ii. passing the thus treated mother liquor through a chromatographic column containing sulfonated polystyrene cation exchange resins cross-coupled with di-vinyl benzene to provide a mixed polyol by-product fraction, a return fraction, and a xylitol-rich fraction,
      iii. removing the mixed polyol by-product fraction from the system,
      iv. returning the return fraction as a portion of the feed solution to the chromatographic column, and
      v. adding the xylitol-rich fraction to the stream feeding the crude crystallization step (d).

6. The method of claim 3, wherein the chromatographic fractionation of step (d) is conducted using at least two columns containing sulfonated polystyrene cation exchange resins cross-coupled with di-vinyl benzene, one of said columns containing the resin in an alkaline earth form and the other of said columns containing the resin in an $Al^{+++}$ or $Fe^{+++}$ form.

7. The process of claim 1 wherein the residual xylitol from the mother liquor from the recrystallization step is combined with the mixture of polyols used as feed solution to the process at a point prior to the crude xylitol crystallization step.

8. The process of claim 1, wherein the crude crystals obtained in step (b) are
   i. washed with water to remove microcrystals of galactitol from the surfaces thereof,
   ii. the crystal washings recovered, and
   iii. the mother liquor from the crude crystallization, and crystal washings, are subjected to a galactitol removal step and then to a xylitol removal step utilizing chromatographic fractionation.

9. The process of claim 8, wherein the mother liquor from the recrystallization step is combined with the mixture of polyols used as feed solution to the process at a point prior to the crude xylitol crystallization step.

10. The process of claim 5, wherein step (h) comprises the steps of
   i. removing galactitol crystals from the combined mother liquors,
   ii. dividing the thus treated mother liquors into two streams,
   iii. passing the first stream through a chromatographic column containing sulfonated polystyrene cation excahnge resins cross-coupled with di-vinyl benzene in the alkaline earth salt form to provide a mixed polyol by-product fraction, a return fraction and a xylitol-rich fraction,
   iv. passing the other portion of liquids through a chromatographic column containing sulfonated polystyrene cation exchange resins cross-coupled with di-vinyl benzene and $Al^{+++}$ or $Fe^{+++}$ form to provide a mixed polyol by-product fraction, a return fraction, and a xylitol-rich fraction,
   v. combining the respective fractions from the two streams,
   vi. removing the mixed polyol by-product from the system,
   vii. returning the return fraction as a portion of the feed solution to the chromatographic column, and
   viii. adding the xylitol-rich fraction to the stream feeding the crude crystallization step.

* * * * *